(12) United States Patent
Wessendorf et al.

(10) Patent No.: US 8,000,804 B1
(45) Date of Patent: Aug. 16, 2011

(54) ELECTRODE ARRAY FOR NEURAL STIMULATION

(75) Inventors: Kurt O. Wessendorf, Albuquerque, NM (US); Murat Okandan, Edgewood, NM (US); David J. Stein, Albuquerque, NM (US); Pin Yang, Albuquerque, NM (US); Joseph Cesarano, III, Albuquerque, NM (US); Jennifer Dellinger, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 1076 days.

(21) Appl. No.: 11/588,905

(22) Filed: Oct. 27, 2006

(51) Int. Cl.
*A61N 1/00* (2006.01)

(52) U.S. Cl. ............. 607/116; 607/53; 607/54; 607/115

(58) Field of Classification Search .............. 607/53–54, 607/115–116
See application file for complete search history.

(56) References Cited

U.S. PATENT DOCUMENTS

| | | | | |
|---|---|---|---|---|
| 3,951,327 | A * | 4/1976 | Snow et al. ................... | 228/121 |
| 4,506,680 | A * | 3/1985 | Stokes ........................... | 607/120 |
| 5,935,155 | A * | 8/1999 | Humayun et al. .............. | 607/54 |
| 6,533,798 | B2 | 3/2003 | Greenberg et al. | |
| 6,974,533 | B2 | 12/2005 | Zhou | |
| 7,027,874 | B1 | 4/2006 | Sawan et al. | |
| 7,079,900 | B2 | 7/2006 | Greenberg et al. | |
| 2002/0161417 | A1* | 10/2002 | Scribner ......................... | 607/54 |
| 2005/0288733 | A1 | 12/2005 | Greenberg et al. | |
| 2006/0036296 | A1* | 2/2006 | Greenberg et al. ............. | 607/54 |
| 2006/0111757 | A9 | 5/2006 | Greenberg et al. | |
| 2006/0173497 | A1 | 8/2006 | Mech et al. | |
| 2007/0112404 | A1* | 5/2007 | Mann et al. .................... | 607/116 |

OTHER PUBLICATIONS

A. M. Feltham et al, "Platinized Platinum Electrodes", Chemical Reviews, vol. 71, pp. 177-193 (1971).
Kevin P. Plunknett et al, "Tape Casting of Fine Alumina/Zirconia Powders for Composite Fabrication", Journal of the American Ceramic Society, vol. 77, No. 8, pp. 2137-2144 (1994).
Thomas Stieglitz et al, "Micromachined, Polyimide-Based Devices for Flexible Neural Interfaces," Biomedical Microdevices, vol. 2, No. 4, 2000, pp. 283-294.
B. Ilic et al, "Preparation and Characterization of Platinum Black Electrodes," Journal of Materials Science, vol. 35 (2000) pp. 3447-3457.
Wentai Liu et al, "A Neuro-Stimulus Chip with Telemetry Unit for Retinal Prosthetic Device," IEEE Journal of Solid-State Circuits, vol. 35 No. 10 Oct. 2000, pp. 1487-1497.
K. Mathieson et al, "Large-Area Microelectrode Arrays for Recording of Neural Signals," IEEE Transactions on Nuclear Science, vol. 51, No. 5, Oct. 2004, pp. 2027-2031.
James D. Weiland and Mark S. Humayun et al, "A Biomimetic Retinal Stinulating Array—Design Considerations," IEEE Engineering in Medicine and Biology Magazine, Sep./Oct. 2005, pp. 14-21.

* cited by examiner

*Primary Examiner* — Niketa I Patel
*Assistant Examiner* — Rex Holmes
(74) *Attorney, Agent, or Firm* — John Hohimer

(57) ABSTRACT

An electrode array for neural stimulation is disclosed which has particular applications for use in a retinal prosthesis. The electrode array can be formed as a hermetically-sealed two-part ceramic package which includes an electronic circuit such as a demultiplexer circuit encapsulated therein. A relatively large number (up to 1000 or more) of individually-addressable electrodes are provided on a curved surface of a ceramic base portion the electrode array, while a much smaller number of electrical connections are provided on a ceramic lid of the electrode array. The base and lid can be attached using a metal-to-metal seal formed by laser brazing. Electrical connections to the electrode array can be provided by a flexible ribbon cable which can also be used to secure the electrode array in place.

32 Claims, 8 Drawing Sheets

FIG. 2A
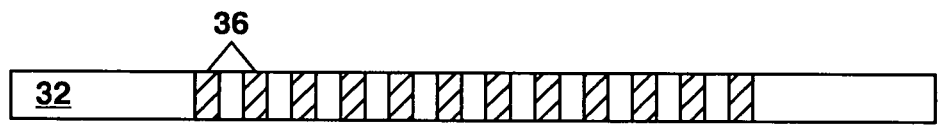
FIG. 2B
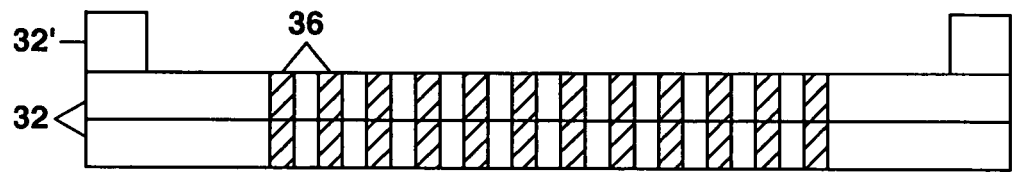
FIG. 2C
FIG. 2D

ELECTRODE ARRAY FOR NEURAL STIMULATION

GOVERNMENT RIGHTS

This invention was made with Government support under Contract No. DE-AC04-94AL85000 awarded by the U.S. Department of Energy. The Government has certain rights in the invention.

FIELD OF THE INVENTION

The present invention relates in general to electrode arrays for neural stimulation, and in particular to a ceramic electrode array package which can be hermetically sealed for use in prosthetic devices including an implantable retinal prosthesis.

BACKGROUND OF THE INVENTION

Efforts are currently underway in a number of groups worldwide to develop an implantable retinal prosthesis to restore at least partial sight to persons suffering from certain forms of blindness due to end-stage photoreceptor degenerative diseases such as age-related macular degeneration and hereditary retinitis pigmentosa. See J. D. Weiland et al., "A Biomimetic Retinal Stimulating Array," *IEEE Engineering in Medicine and Biology Magazine*, pp. 14-21, September/October 2005 for a recent review of progress in this area. Such retinal prostheses, which are currently being developed, are based on the electronic transfer of visual information from a camera located in front of the eye to receiver electronics which will be implanted within or adjacent to the eye. The receiver electronics will then feed the visual information in pixelized form to an electrode array which is located either directly in front of the retina (epiretinal) or beneath the retinal tissue (sub-retinal). Electrical currents from the electrode array will stimulate neural tissue (e.g. ganglion cells) in the retina to generate a visual perception of spots of light (also termed phosphenes) corresponding to the pixelized visual image, with the goal of being able to restore a measure of sight to a blind person.

Current retinal prosthesis designs that incorporate inner-eye electronics use soft-package techniques to protect the electronics from the corrosive environment of the inner eye. The electronics are typically attached to polymer electrode arrays that have plated platinum electrodes driven via metallized traces. Such devices have a limited operational lifetime of weeks to months, and are also limited in the number of electrodes that can be fabricated using this technology.

What is needed is a hermetic package that will allow a much longer operational lifetime and which can include a much larger number of electrodes up to one thousand or more individually addressable electrodes.

The present invention represents an advance in the art by providing an electrode array for neural stimulation which allows up to one thousand or more individually addressed electrodes to be contained within a two-part ceramic package which can be hermetically sealed. An electronic circuit such as a demultiplexer circuit can be located inside the two-part ceramic package to reduce the number of signal lines needed for operation of the electrode array.

These and other advantages of the present invention will become evident to those skilled in the art.

SUMMARY OF THE INVENTION

The present invention relates to an electrode array for neural stimulation which comprises a two-part ceramic package having a ceramic base and a ceramic lid. The ceramic base and the ceramic lid each have a pair of major surfaces, with at least one of the ceramic base and the ceramic lid having a ceramic lip extending outward therefrom to define an interior region between the ceramic base and the ceramic lid. The ceramic lid includes a plurality of electrical connections (also termed vias) extending between the pair of major surfaces thereof; and the ceramic base includes a plurality of electrodes extending between the pair of major surfaces thereof. An electronic circuit is located within the interior region to receive electrical input signals conducted through the plurality of electrical connections and to generate therefrom electrical output signals which are communicated to the plurality of output electrodes for use in neural stimulation. The electrical input signals can be multiplexed to reduce the number of electrical connections to the two-part ceramic package; and the electronic circuit can be a demultiplexer circuit.

The major surface of the ceramic base outside of the interior region can be a curved surface when the electrode array is to be used as a part of a retinal prosthesis. The two-part ceramic package can also have a circular shape in plan view.

The ceramic base can be attached to the ceramic lid by a metal-to-metal seal formed therebetween. Electrical interconnections are provided between the electrical connections in the ceramic lid and a plurality of contact pads on the electronic circuit, or on the major surface of the ceramic base inside the interior region.

The output electrodes can comprise metal (e.g. platinum, gold, silver, iridium, molybdenum); and can be overcoated with a layer of platinum on an exposed end thereof outside of the interior region. The output electrodes can also comprise sintered metal electrodes, or a sintered mixture of ceramic and metal.

The ceramic base and the ceramic lid can be formed from a ceramic material which comprises 50-80 percent by volume zirconium oxide, and about 50-20 percent by volume aluminum oxide.

The present invention also relates to an electrode array for neural stimulation which comprises a ceramic base having a first major surface and a second major surface, with the first major surface being curved, and with a ceramic lip located about a curved edge of the second major surface and extending towards the first major surface, and with a plurality of electrodes arranged in a two-dimensional array and extending through the ceramic base between the first and second major surfaces; a ceramic lid having a plurality of electrical connections extending therethrough, with the ceramic lid being attachable to the ceramic base to form a hermetically-sealed interior region; and an electronic circuit (e.g. a demultiplexer circuit) located within the hermetically-sealed interior region. The electronic circuit comprises a plurality of input ports and a plurality of output ports, with the input ports being connected to the electrical connections in the ceramic lid, and with the output ports being connected to the electrodes in the ceramic base to provide electrical output signals to the electrodes for neural stimulation in response to electrical input signals provided to the input ports of the electronic circuit.

The ceramic base and ceramic lid can both be circular in shape with a diameter of a few millimeters (e.g. 4-10 mm, and preferably about 5 mm). The ceramic base and the ceramic lid can also comprise a ceramic material which further comprises 50-80 percent by volume zirconium oxide, and 50-20 percent by volume aluminum oxide. For use in a retinal prosthesis, the first major surface of the electrode array can have a surface radius of curvature (e.g. about 25 mm) which is adapted to provide contact with an inner surface of a human retina.

The electrodes in the electrode array can comprise metal. The electrical connections in the ceramic lid can also comprise metal (e.g. platinum, gold, silver, iridium, molybdenum). In some embodiments of the present invention, the electrodes can comprise sintered metal electrodes (e.g. sintered platinum), while in other embodiments of the present invention, the electrodes can comprise a sintered mixture of ceramic and metal (also known as cermet). The output electrodes can be overcoated with a layer of platinum on at least one end thereof.

Each output port in the electrode array can be connected to one of the electrodes in the ceramic base by solder. Each input port can also be connected to one of the electrical connections in the ceramic lid by solder. In other embodiments of the present invention, the input ports can be connected to the electrical connections in the ceramic lid by an electrically-conductive epoxy, by an electrically-conductive spring or by a deformable metal pin. In yet other embodiments of the present invention, the input ports can be connected to the electrical connections in the ceramic lid via a contact pad formed on the second major surface of the ceramic body.

The ceramic lid can be attached to the ceramic base by a metal annulus formed on the ceramic lip and another metal annulus formed on the ceramic lid, with the two metal annuluses being brazed together (e.g. by laser brazing). Alternately, the ceramic lid can include another ceramic lip extending outward from a major surface thereof towards the ceramic body so that the metal annulus on the ceramic lid can be formed on this ceramic lip.

Additional advantages and novel features of the invention will become apparent to those skilled in the art upon examination of the following detailed description thereof when considered in conjunction with the accompanying drawings. The advantages of the invention can be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several aspects of the present invention and, together with the description, serve to explain the principles of the invention. The drawings are only for the purpose of illustrating preferred embodiments of the invention and are not to be construed as limiting the invention. In the drawings:

FIGS. 2A-2H show schematic cross-section views to illustrate certain steps for fabricating the electrode array of FIGS. 1A and 1B.

DETAILED DESCRIPTION OF THE INVENTION

Figure 1A:
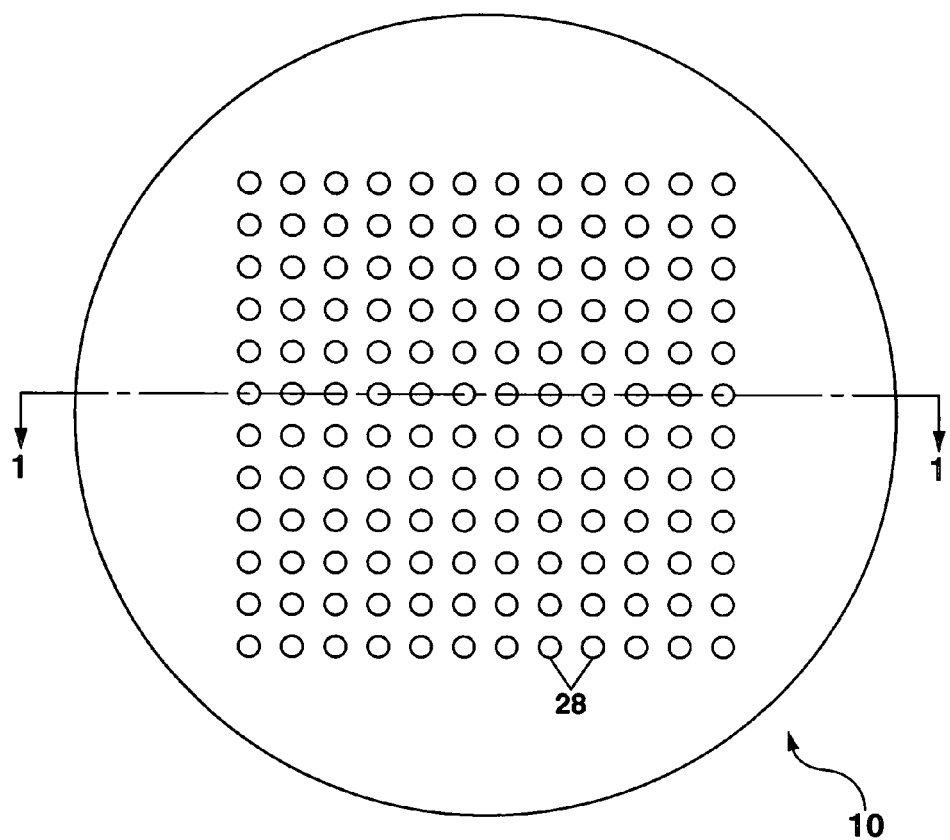
FIG. 1A shows a schematic plan view of an example of an electrode array according to the present invention.
Figure 1B:
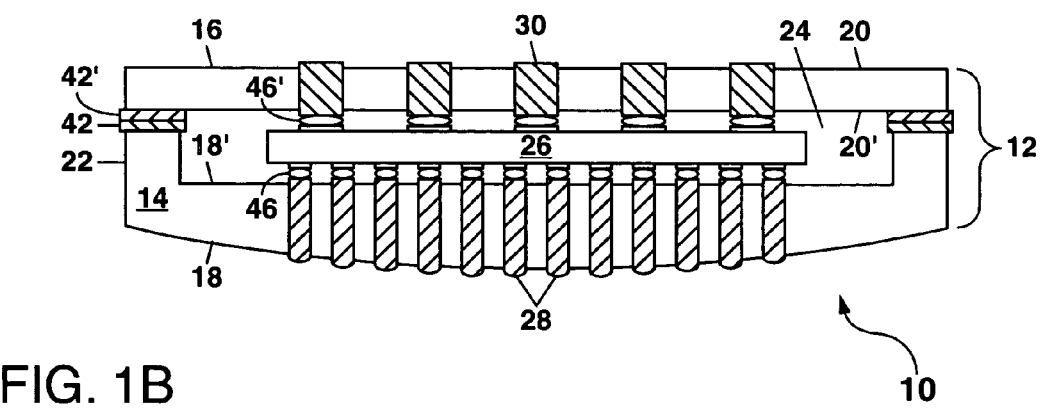
FIG. 1B shows a schematic cross-section view of the electrode array along the section line 1-1 in FIG. 1A.

Referring to FIGS. 1A and 1B, there is shown a schematic plan view and a schematic cross-section view, respectively, of a first example of an electrode array 10 formed according to the present invention. The electrode array 10, which has applications for neural stimulation in a retinal prosthesis, comprises a two-part ceramic package 12 which further comprises a ceramic base 14 and a ceramic lid 16. The ceramic base 14 comprises a pair of major surfaces 18 and 18'; and the ceramic lid 16 comprises another pair of major surfaces 20 and 20'. A ceramic lip 22 extends upward from the ceramic base 14 towards the ceramic lid 20 to form in combination with the major surfaces 18' and 20' an interior region 24 wherein an electronic circuit 26 can be located. The electronic circuit 26 is useful to electrically address a plurality of electrodes 28 and to provide electrical output signals to the various electrodes 28 as required for neural stimulation to form an image on a user's retina using information provided as electrical inputs to the electrode array 10.

Figure 3:
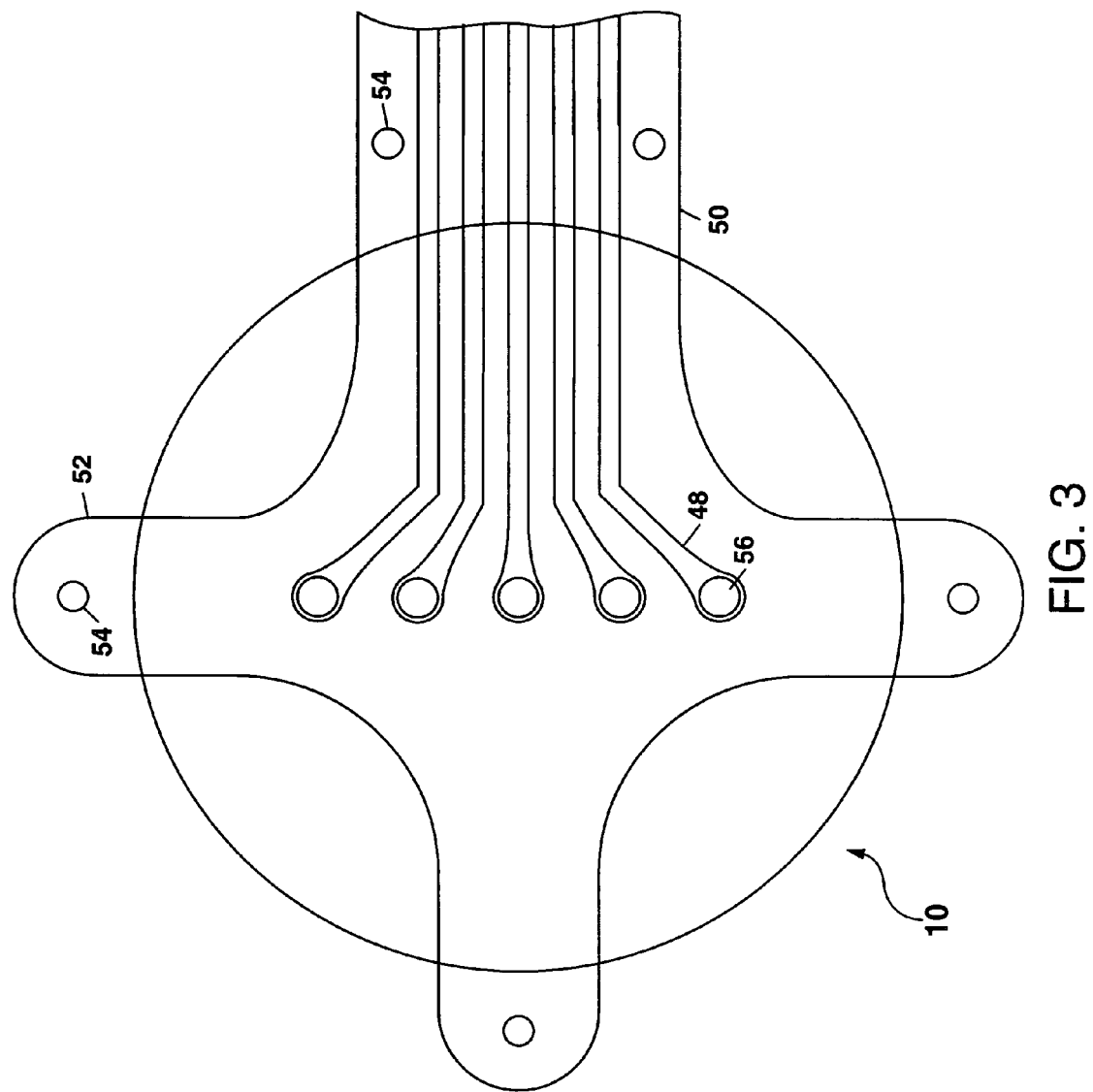
FIG. 3 shows a schematic plan view of the electrode array of FIGS. 1A and 1B with a flexible ribbon cable attached which can also be used to secure the electrode array to a user's retina.

Electrical power and input signals from a camera and associated transmitter/receiver electronic circuitry (not shown) can be provided to the electronic circuit 26 via a ribbon cable (also termed a flex cable) which can be connected to a plurality of electrical vias 30 which extend through the ceramic lid 16 (see FIG. 3). The camera and transmitter circuitry can be located outside a user's eye, with the receiver circuitry being located either outside the eyeball, or therein and connected to the electrode array 10 via the ribbon cable. Further details of retinal prostheses including transmitter/receiver electronic circuitry can be found in U.S. Pat. Nos. 5,935,155; 7,027,874 and 7,079,900; in U.S. Published Patent Application Nos. 2005/0288733; 2006/0036296; and 2006/0111757; in the aforementioned article by J. D. Weiland et al., entitled "A Biomimetic Retinal Stimulating Array," and in another article by W. Liu et al., "A Neuro-Stimulus Chip with Telemetry Unit for Retinal Prosthetic Device," *IEEE Journal of Solid-State Circuits*, vol. 35, pp. 1487-1497, October 2000. Each of the above references is incorporated herein by reference.

To greatly reduce the number of electrical vias 30 and hence the number of external wires (e.g. in a ribbon cable) that must be connected to the electrode array 10, multiplexing of the electrical input signals can be used. The multiplexed electrical input signals contain information to indicate the addresses of particular electrodes 28 to be electrically activated at a particular time, and characteristics of the electrical output signal (generally a biphasic current signal) to be applied to each activated electrode 28 including pulse amplitude, pulse width, interphase delay between positive and negative pulses forming the biphasic current signal, and frequency of the pulses. The electronic circuit 26, which can be a demultiplexer circuit, then demultiplexes the information in the electrical input signals to generate the electrical output signals for the electrode array 10 to produce a sensed image for the user which corresponds to a scene viewed by the camera.

Demultiplexer circuits for use in retinal prostheses are well known in the art and need not be described herein in great detail. The demultiplexer circuit 26 is in chip form and preferably provides a demultiplexing (i.e. demux) ratio of 4 to 1 or greater.

Fabrication of the electrode array 10 of the present invention can be understood with reference to FIGS. 2A-2H which illustrate in schematic cross-section view a series of steps for forming the electrode array 10 in the example of FIGS. 1A and 1B. Although FIGS. 2A-2H describe the fabrication of the ceramic base 14 for a single electrode array 10, those skilled in the art will understand that a plurality of ceramic bases 14 can be batch fabricated from the same "green" ceramic tapes 32. Other types of machining processes can also be used to form the ceramic base 14, including molding (e.g. pressing or injection molding a "green" ceramic material). Additionally, those skilled in the art will understand that the teachings and processes described with respect to FIGS. 2A-2H can also be applied to form the ceramic lid 16.

In FIG. 2A, a "green" ceramic tape 32 is provided which is punchable with a thickness of, for example, about 100 microns (μm) after drying. The "green" ceramic tape 32 can be formed using conventional tape casting technology, or can be procured commercially. The "green" ceramic tape 32 can comprise a bio-inert and/or biocompatible ceramic material such as alumina (i.e. aluminum oxide), zirconia (i.e. zirconium oxide), mullite, hydroxyapatite, or combinations thereof.

As an example, a composite "green" ceramic tape can be formed from alumina and zirconia, with 50-80 percent by volume zirconia and 50-20 percent by volume alumina. The exact percentages of alumina and zirconia can be selected to provide a coefficient of thermal expansion which substantially matches the materials used to form the electrodes 28 in the base 14, and the vias 30 in the lid 16. When the electrodes 28 and vias 30 comprise platinum, for example, the composite ceramic can comprise about 65 percent by volume zirconia and 35 percent by volume alumina. Since alumina has a lower coefficient of thermal expansion than platinum, and zirconia has a higher coefficient of thermal expansion than platinum, then this composition with about 65 percent by volume zirconia and 35 percent by volume alumina will provide substantially the same coefficient of thermal expansion as platinum. This can reduce the possibility of forming any microcracks between the electrodes 28 or vias 30 which could otherwise affect the hermeticity of the electrode array 10. When other biocompatible metals (e.g. iridium or gold) or a cermet is used to form the ceramic base 14, or ceramic lid 16, or both, then the alumina/zirconia composition can be similarly adjusted to provide a coefficient of thermal expansion which is substantially the same for the ceramic base 14 and the electrodes 28 therein, or for the ceramic lid 16 and the vias 30 therein.

The alumina and zirconia or any other combination of the bio-inert and/or biocompatible ceramic materials described above can be milled to form fine powders with a micron to sub-micron size. The fine powders can be seived to remove any agglomerates and then mixed together with a solvent, dispersant, binder and plasticizer to form a slurry which can be filtered to again remove any agglomerates. The slurry can be de-aired to remove any bubbles and then can be tape cast to form a "green" ceramic tape as shown in FIG. 2A. The formation of "green" ceramic tape comprising alumina, zirconia or both is well-known in the art (see e.g. K. P. Plucknett et al., "Tape Casting of Fine Alumina/Zirconia Powders for Composite Fabrication," *Journal of the American Ceramic Society*, vol. 77, pp. 2137-2144, 1994, which is incorporated herein by reference).

In FIG. 2B, the "green" ceramic tape 32 can be punched or laser drilled to form an array of openings 34 having, for example, a diameter of 50-100 μm and spaced apart by a center-to-center distance of, for example, 100-250 μm. The openings 34 can be provided in an array which can be, for example, square (see FIG. 1A), or hexagonal, or arbitrarily-shaped with up to one thousand or more total openings 34 for the electrode array 10. The exact size and spacing of the openings 34 will depend upon the total number of electrodes 28 required for the electrode array 10 and an area of the ceramic base 14 into which the electrodes 28 must fit.

In FIG. 2C, the openings 34 can be filled with a paste or ink 36 comprising, for example, a biocompatible metal such as gold, silver, platinum, iridium, or a combination thereof. The paste or ink 36, which comprises microscopic metal particles, can optionally include microscopic ceramic particles (e.g. alumina or zirconia or both) to form electrodes 28 which will comprise a sintered mixture of ceramic and metal (also termed cermet).

In FIG. 2D, after filling the openings 34 in a plurality of "green" ceramic tapes 32 with the paste or ink 36, the tapes 32 can be stacked up in preparation for co-firing to provide a predetermined thickness for the ceramic base 14. One or more additional punched "green" ceramic tapes 32' with an annular shape can also be stacked up to form the ceramic lip 22 for the electrode array 10.

After the tapes 32 and 32' have been stacked up and clamped together, the tapes 32 and 32' can be co-fired at about 500° C. to burn away the binder therein and then at a temperature in the range of 850-1450° C. to densify the ceramic material and to sinter the paste or ink 36 used to form the electrodes 28. The electrodes 28 can be either sintered metal electrodes or cermet electrodes depending upon whether or not ceramic particles are added to the paste or ink 36. Those skilled in the art will understand that a certain amount of shrinkage (e.g. 10-15%) can occur in the dimensions of the ceramic base 14 upon co-firing; and that this must be taken into account in sizing the "green" ceramic tapes 32 and 32' to provide predetermined dimensions for the co-fired ceramic base 14 and lid 16.

Figure 2E:
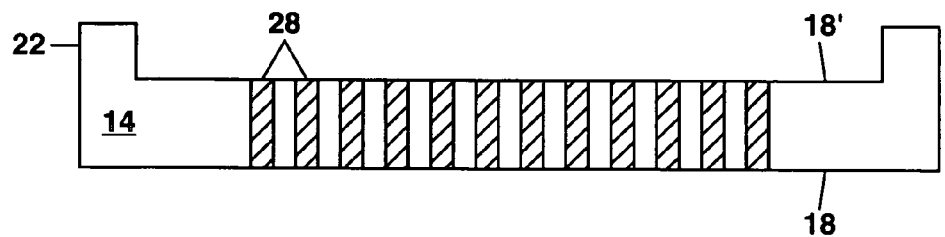
Figure 2F:
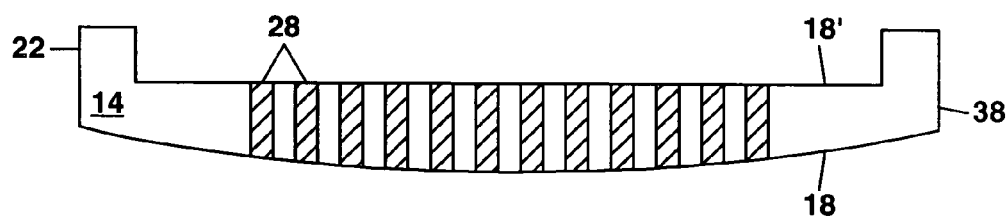

The ceramic base 14 after co-firing is shown in FIG. 2E with a lower major surface 18 and an upper major surface 18' each being substantially planar, at least in the vicinity of the electrodes 28. In FIG. 2F, an ultra-precision diamond turning machine (i.e. a diamond lathe) can be used to remove material from the lower major surface 18 to convert this surface 18 into a curved surface with a radius on the order of 25 millimeters. The exact radius of curvature for the lower major surface 18 will be sized to substantially match the curvature of an inner surface of a human retina with which the electrode array 10 is to be used. This helps to provide an intimate contact with the retina for neural stimulation of retinal cells to generate phosphenes using electrical currents provided through the various electrodes 28. Additional surfaces of the ceramic base 14 can be machined or polished, if needed, to remove any surface irregularities and to provide a substantially circular outer sidewall 38 for the ceramic base 14.

Figure 2G:
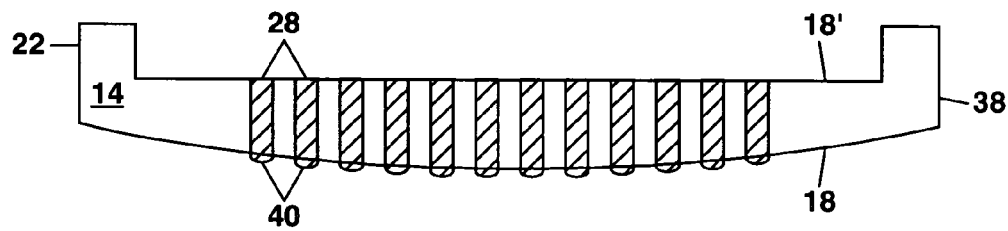

In FIG. 2G, the exposed ends of the electrodes 28 can be platinized with an overcoated layer 40 of platinum. This can be done by plating the ends of the electrodes 28 on the curved lower major surface 18 with a layer 40 of platinum in the form of platinum black or preferably platinum gray up to several tens of microns thick. The platinum black or platinum gray provides an increased surface area for each electrode 28 without necessarily increasing the electrode's size. This increased surface area reduces the electrical impedance of the electrodes 28 when placed in contact with the retina.

The use of an overcoated layer 40 of platinum can also allow the use of an alternative metals such as molybdenum for the electrodes 28. The molybdenum can be isolated from exposure to tissues and fluids within the eye by the overcoated layer 40 of platinum.

Those skilled in the art will understand that the terms "platinum black" and "platinum gray" refer to platinum which has a black or gray visual appearance due to a nanogranular structure (also termed a cauliflower structure) of the deposited platinum when deposited over a relatively large surface area having lateral dimensions of several tens of microns or more.

Platinum black can be electrodeposited in an electroplating cell from a solution of chloroplatinic acid and water with added lead acetate (e.g. 1-3.5% chloroplatinic acid and 0.005-0.08% lead acetate with an electrical current of 10-200 mA·cm$^{-2}$). Platinum gray can be electrodeposited from the same solution without the lead acetate. The use of platinum gray for the layer 40 is preferred since this eliminates the possibility for the desorption of any lead from the layer 40.

The preparation of platinum black and platinum gray is disclosed in U.S. Pat. No. 6,974,533 and in the following articles: A. M. Feltham et al., "Platinized Platinum Electrodes," *Chemical Reviews*, vol. 71, pp. 177-193, 1971; B. Ilic et al., "Preparation and Characterization of Platinum Black Electrodes," *Journal of Materials Science*, vol. 35, pp. 3447-3457, 2000; K. Mathieson et al., "Large-Area Microelectrode Arrays for Recording of Neural Signals," *IEEE Transactions on Nuclear Science*, vol. 51, pp. 2027-2031, October 2004. Each of the above references is incorporated herein by reference.

Figure 2H:
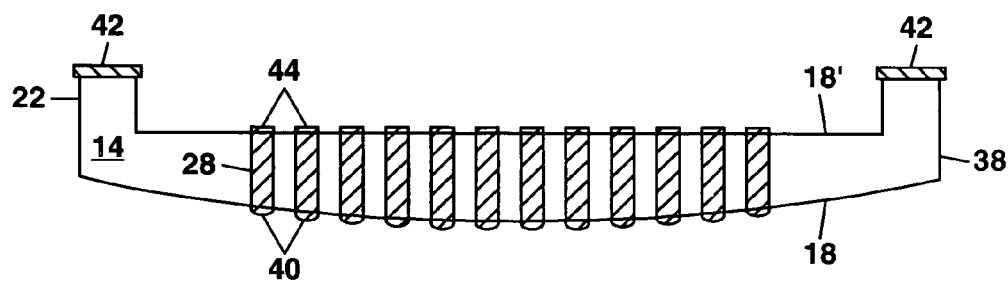

In FIG. 2H, a metal annulus 42 can be deposited on top of the ceramic lip 22 for later use in sealing the ceramic base 14 to the ceramic lid 16. The metal annulus 42 can comprise one or more layers of biocompatible metals or metal alloys including titanium, platinum, gold, silver, nickel and combinations thereof with an overall thickness of up to a few tens of microns. The metal annulus 42 can be applied directly with a printing technique. Alternately, the metal annulus 42 can be formed by masking the major surfaces 18 and 18' and initially evaporating or sputter depositing a metal seed layer (e.g. titanium or nickel) on top of the ceramic lip 22, and then building up the metal annulus 42 by electroplating.

Figure 6:
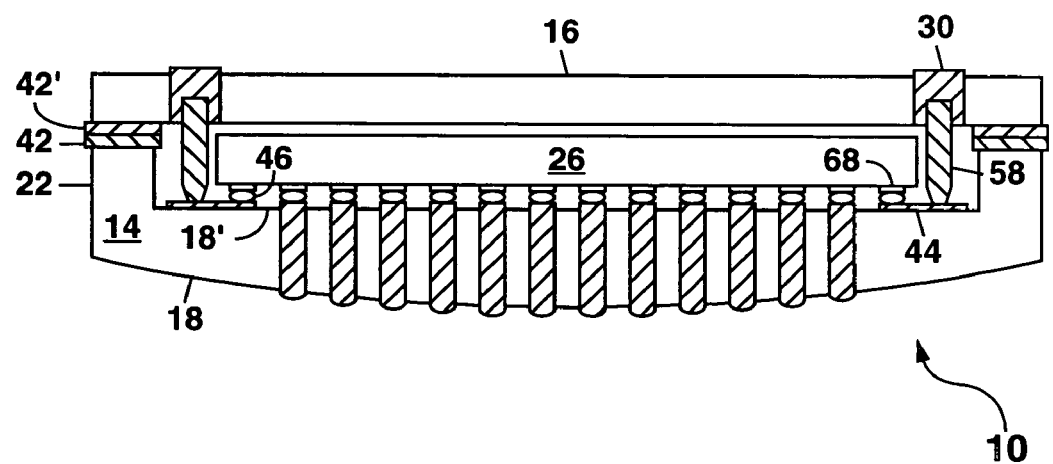
FIG. 6 shows a schematic cross-section view of a third example of the electrode array of the present invention.

One or more layers of metal (e.g. aluminum, gold, titanium, nickel, etc.,) can also be deposited on the upper major surface 18' and on the exposed ends of the electrodes 28 on this side of the ceramic base 14 as shown in FIG. 2H to form contact pads 44 for use in attaching the electronic circuit 26 to the ceramic base 14, or to provide electrical interconnections to the electronic circuit 26 from the ceramic lid 16 (see FIG. 6). The contact pads 44 can be deposited at the same time as the metal annulus 42 is formed by electroplating, or can alternately deposited by printing, evaporation or sputtering. The contact pads 44 can have a thickness of, for example, up to about 1 μm.

The ceramic lid 16 shown in the example of FIG. 1B can be formed in a manner similar to the ceramic base 14 as described with reference to FIGS. 2A-2E using the same "green" ceramic tape 32 which can be punched to form a plurality of openings 34 therein. A smaller number of openings 34 are needed for the ceramic lid 16; and the openings can be of a larger size (e.g. 100-200 μm diameter).

The openings 34 in the ceramic lid 16 can be filled with a paste or ink 36 comprising gold, silver, platinum, or a combination thereof as previously described with reference to FIG. 2B. In some cases, the vias 30 can comprise a cermet. Then one or more layers of the "green" ceramic tape 32 can then be stacked up to a predetermined overall thickness and co-fired. Another ceramic lip 22' (see FIG. 4) can optionally be formed on the ceramic lid 16 by providing additional punched "green" ceramic tapes 32' having an annular shape.

After co-firing of the ceramic lid 16, another metal annulus 42' can be deposited on a major surface 20' of the ceramic lid 16 (see FIG. 1B) for use in sealing the ceramic lid 16 to the ceramic base 14. This can be done as previously described with reference to FIG. 2H using one or more layers of biocompatible metals or metal alloys (e.g. comprising titanium, platinum, gold, nickel or combinations thereof) which can be printed on or plated up to an overall thickness of up to a few tens of microns. Contact pads 44 can also be formed on one or both major surfaces of the ceramic lid 16 by printing, electroplating, evaporation or sputtering as previously described with reference to FIG. 2H. Certain of the contact pads 44 which will be hermetically sealed within the electrode array 10 do not necessarily need to be formed from a biocompatible metal; whereas other contact pads 44, which will be on an outside major surface of the ceramic lid 16 after fabrication of the electrode array 10 is completed, are preferably formed from a biocompatible metal such as platinum, gold, silver, titanium, or a combination thereof.

Returning to FIGS. 1A and 1B, an electronic circuit 26 is provided for use with the electrode array 10. The electronic circuit 26 shown in FIG. 1B has a plurality of contact pads on a top side of the circuit 26 which form input ports for the circuit 26, and a plurality of contact pads on a bottom side of the circuit 26 which form output ports. Those skilled in the art will understand that the contact pads on the top side of the electronic circuit 26 can be connected to vias (not shown) which provide a conducting path from the top side of the circuit 26 to the bottom side thereof where a plurality of integrated electronic devices including transistors and resistors can be located for processing electrical input signals and generating electrical output signals.

In FIG. 1B, the electronic circuit 26, which generally comprises a demultiplexer circuit, can be attached to the ceramic base 14 using a plurality of solder balls 46 which can be located between the contact pads on the bottom side of the electronic circuit 26 and the electrodes 28. Each solder ball 46 can comprise, for example, a lead-tin solder with a predetermined eutectic temperature. The electronic circuit 26 can be initially soldered to the ceramic base 14 to allow testing of the electrical output signals provided to each electrode 28 by the electronic circuit 26. Electrical signals and power can be fed into the electronic circuit 26 using a probe card, and the electrical output signals from each electrode 28 can be monitored with another probe card.

The ceramic lid 16 can then be attached to the top side of the electronic circuit 26 using additional solder balls 46' located between the electrical connections 30 and contact pads on the top side of the electronic circuit 26. The solder balls 46' can have a solder composition (e.g. a lead-tin solder) with a higher eutectic temperature than that for the solder balls 46 which attach the circuit 26 to the ceramic base 14.

In other embodiments of the present invention, the electronic circuit 26 can be attached to the ceramic base 14 and lid 16 in a single soldering step. In yet other embodiments of the present invention, an electrically-conductive epoxy (e.g. a silver loaded epoxy) can be substituted for the solder balls 46 and 46' in FIG. 1B to attach the electronic circuit 26 to the ceramic base 14 and lid 16.

The electronic circuit 26 can be hermetically sealed within the electrode array 10 by forming a metal-to-metal seal between the ceramic base 14 and ceramic lid 16. This can be done by brazing the two metal annuluses 42 and 42' around the periphery of the electrode array 10, or alternately using ultrasonic bonding or diffusion bonding. The use of a laser for brazing the two metal annuluses 42 and 42' to form the metal-to-metal seal is particularly advantageous since this can localize heating to an area where the metal-to-metal seal is being formed and can thereby prevent excessive heating of the electronic circuit 26. To do this, the electrode array 10 can be held in a fixture which slowly rotates the two metal annuluses 42 and 42' past a focused laser beam (e.g. from a Nd:YAG or $CO_2$ laser) to form a laser brazed metal-to-metal seal around the periphery of the electrode array 10.

External wires 48 contained in a flexible ribbon cable 50 can be attached to the electrical connections 30 on a top side of the ceramic lid 16 as shown in the schematic plan view of FIG. 3. The ribbon cable 50 is used to provide electrical power and input signals to the electronic circuit 26, and can also be used to attach the electrode array 10 and ribbon cable 50 to a user's retina using a plurality of support tabs 52 which have openings 54 therethrough. This attachment can be performed, for example, using titanium tacks or sutures.

Although FIG. 3 shows only a few wires 48 in the flexible ribbon cable 50, the exact number of wires 48 can be much larger and will depend upon the number of input ports for electrical power and input signals which are required to operate the electronic circuit 26. Generally, the number of wires 48 will be only a small fraction (e.g. ¼) of the number of electrodes 28, with the exact number of wires 48 being dependent upon the level of multiplexing of the electrical input signals provided to the electronic circuit 26.

In FIG. 3, each wire 48 in the ribbon cable 50 can be attached to the electrode array 10, for example, by using a gold ball bond 56 (also termed a bump bond). The gold ball bond can be formed by thermosonically bonding an exposed portion of a wire 48 in the ribbon cable 50 and at the same time to one of the electrical connections 30 using a conventional thermosonic ball bonding machine. The exposed portion of the wire 48 being bonded to the electrical connection 30 can have an opening therethrough so that the gold ball bond 56 contacts both the wire 48 and the electrical connection 30 and is thermosonically welded thereto. The fabrication of polyimide- or silicon-insulated ribbon cable and the attachment of such ribbon cable to neural electrode arrays is well-known in the art and need not be described herein in great detail. See e.g. T. Stieglitz et al., "Micromachined, Polyimide-Based Devices for Flexible Neural Interfaces," *Biomedical Microdevices*, vol. 2, pp. 283-294, 2000 which is incorporated herein by reference.

Figure 4:
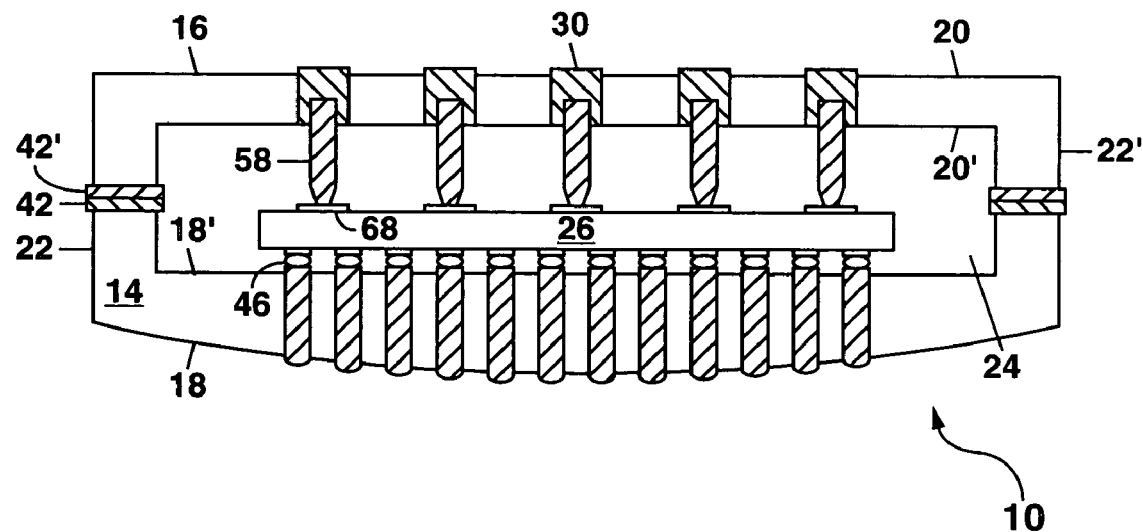
FIG. 4 shows a schematic cross-section view of a second example of the electrode array of the present invention.

FIG. 4 schematically illustrates in cross-section view a second example of the electrode array 10 of the present invention. In the example of FIG. 4, the ceramic base 14 can be formed as previously described with reference to FIGS. 2A-2H, with the electronic circuit 26 being attached to the ceramic base 14 using a plurality of solder balls 46 as previously described with reference to FIG. 1B. In the example of FIG. 4, a plurality of electrical interconnections between the ceramic lid 16 and the electronic circuit 26 are made using deformable metal pins 58. The metal pins 58 can comprise, for example, gold, silver, copper, aluminum or a combination thereof (e.g. a core of silver, copper or aluminum overcoated with a layer of gold).

Figure 5A:
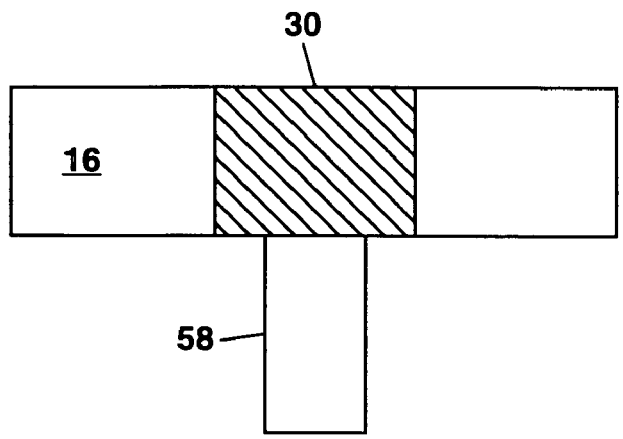
FIGS. 5A-5C shows schematic cross-section views of a portion of the ceramic lid with a deformable metal pin attached thereto to illustrate various ways of forming the metal pins.

The deformable metal pins 58 can be attached to the ceramic lid 16, for example, by drilling holes partway through each electrical connection 30 (e.g. with a laser or mechanical drill) and then inserting the pins 58 into the holes. The pins 58, which can be formed from pre-cut lengths of wire or cut to size after insertion, can be held in place by an interference fit, by solder, or by an electrically-conductive epoxy. Alternately, the pins 58 can be electroplated outward from the electrical connections 30 using a mask placed over the major surface 20' with openings therethrough to define the dimensions of the pins 58. FIG. 5A shows a schematic cross-section view of a portion of the ceramic lid 16 with an electrical connection 30 having an electroplated pin 58 formed thereon.

Figure 5B:
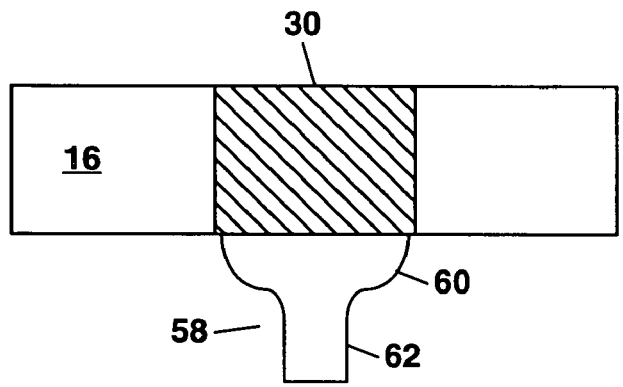

Other types of pins 58 can be used for practice of the present invention. As an example, the pins 58 can comprise a thermosonic gold ball bond 60 formed onto each electrical connection 30 with a length of trailing gold wire 62. This can be done with a conventional thermosonic ball bonding machine and is schematically illustrated in the cross-section view of FIG. 5B.

Figure 5C:
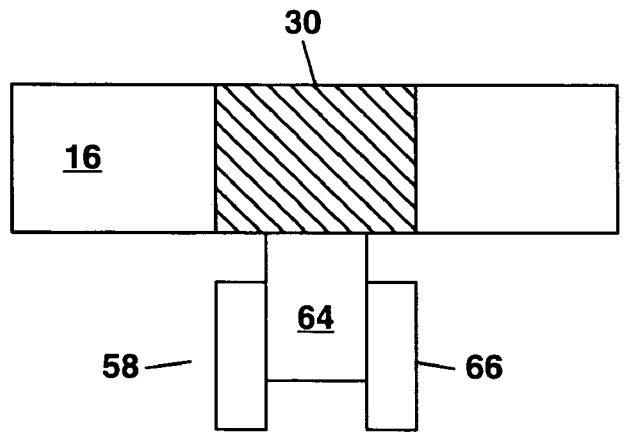

As another example, the pins 58 can comprise a metal core 64 which can be electroplated onto the electrical connection 30, or alternately formed as shown in FIG. 5A. In this example, a metal sleeve 66 (e.g. a length of gold capillary tubing, or a gold bead, or a solder preform) is inserted partway over the metal core 64 with a snug fit as schematically illustrated in the cross-section view of FIG. 5C. When this pin 58 is urged against a contact pad for an input port 68 on the electrical circuit 26 in FIG. 4, the metal sleeve 66 will be urged towards the electrical connection 30 slightly while still bridging a gap between the electrical connection 30 and the electronic circuit 26 to form a low-impedance electrical interconnection therebetween. When the metal sleeve 66 comprises a solder preform, a heating step can be used to bond each pin 58 to the electronic circuit 26.

In each case above, an initial length of the pins 58 can be sized to be slightly larger than the distance between the electrical connections 30 and the electronic circuit 26 which the ceramic lid 16 is attached to the ceramic base 14. This will ensure that each pin 58 contacts one of the contact pads on the electronic circuit 26 and is deformed to provide sufficient contact force to provide a low-impedance electrical interconnection therebetween. A fixture (e.g. a clamp) can be used to press the ceramic lid 16 against the ceramic base 14 to deform or shorten the pins 58 as they come into contact with the electronic circuit 26 and to hold the electrode array 10 together while the base 14 and lid 16 are laser brazed together.

The pins 58 can also be soldered directly to the electronic circuit 26, if desired, by providing a solder preform (not shown) at the location of each input port 68 on the electronic circuit 26 so that the pins 58 press against the solder preforms. The solder preforms should preferably have a lower eutectic temperature than the solder balls 46 used to attach the circuit 26 to the ceramic base 14. A heating step can then be used to momentarily heat the solder preforms to or above their eutectic temperature and thereby bond the pins 58 to the input ports 68.

FIG. 6 schematically illustrates in cross-section view a third example of the electrode array 10 of the present invention which can be used when the electronic circuit 26 has its input ports and output ports on only one side of the circuit 26. In this case, each input port 68 of the electronic circuit 26 can be connected to a contact pad 44 formed on the upper major surface 18' of the ceramic base 14. This can be done using a solder ball 46 as shown in FIG. 6. The contact pad 44, which can be formed as described previously with reference to FIG. 2H, can be connected to one of the electrical connections 30 in the ceramic lid 16 by a deformable metal pin 58. The metal pin 58 can be attached to the electrical connection 30 and urged against the contact pad 44 when the lid 16 is put into place. Alternately, one end of the metal pin 58 can be attached to the contact pad 44, and the other end of the pin 58 can be pressed against the electrical connection 30 when the lid 16 is positioned over the ceramic base 14.

A free end of each pin 58 can be secured in place with an electrically-conductive epoxy or solder. This can be done, for example, by providing the electrically-conductive epoxy or a solder preform (not shown) between the free end of each pin 58 and one of the contact pads 44 or electrical connections 30. With the ceramic base 14 and lid 16 clamped together, the electrically-conductive epoxy can be cured, or a heating step can be provided to momentarily heat the solder preform to or above its eutectic temperature.

Figure 7:
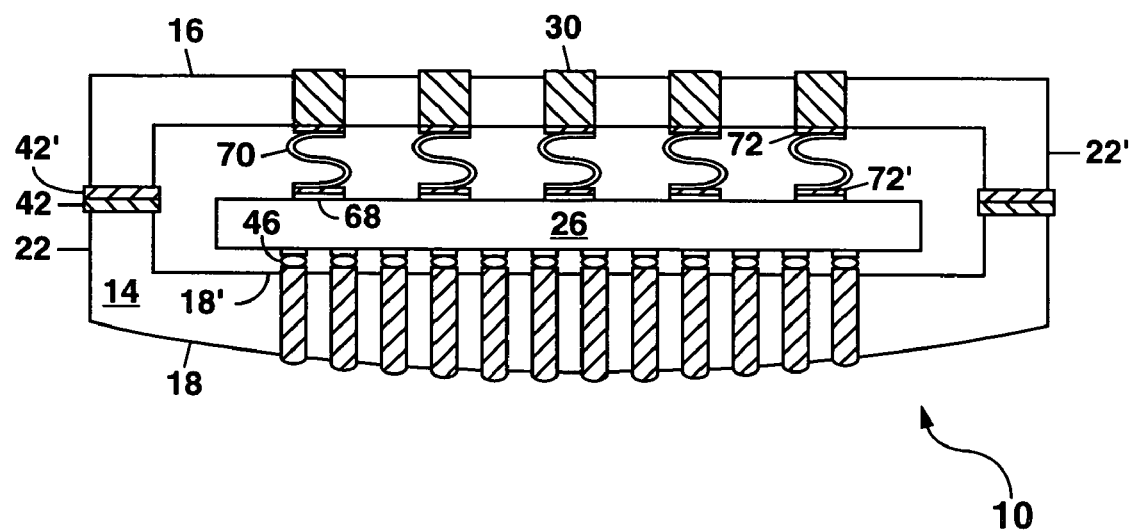
FIG. 7 shows a schematic cross-section view of a fourth example of the electrode array of the present invention.

FIG. 7 is a schematic cross-section view of a fourth example of the electrode array 10 of the present invention. In this fourth example of the present invention, the electronic circuit 26 can be attached to the ceramic base 14 using a plurality of solder balls 46 as described previously with reference to FIG. 1B. A plurality of electrically-conductive springs 70 can be used to form electrical interconnections between the input ports 68 on the electronic circuit 26 and the electrical connections 30 on the ceramic lid 16. The springs 70 can comprise flat lengths of metal (e.g. platinum, gold, silver, copper, aluminum, etc.) which can be bent into an S shape as shown in FIG. 7, or alternately into a Z shape.

The springs 70 can be attached to the ceramic lid 16 using solder preforms 72. The springs 70 can be initially attached to the ceramic lid 16 while the lid 16 is separated from the ceramic base 14 so that a relatively high eutectic temperature can be used for the solder preforms 72. Additional solder preforms 72' with a eutectic temperature lower than that of the solder balls 46, which are used to attach the electronic circuit 26 to the ceramic base 14, can then be provided between the springs 70 and the input ports 68 on the electronic circuit 26. The ceramic lid 16 can then be positioned over the ceramic base 14 and clamped in place while a heating step is used to momentarily heat the solder preforms 72' to or above their eutectic temperature to bond the springs 70 to the electronic circuit 26. While the lid 16 and base 14 are clamped in place, a hermetic seal can be formed around the periphery of the electrode array 10 by laser brazing as previously described. Those skilled in the art will understand that, although the springs 70 in FIG. 7 are shown as being S-shaped, other shapes for the springs 70 can be used.

Although the ceramic base 14 and the ceramic lid 16 have been formed by co-firing, in other embodiments of the present invention, one or both of these ceramic parts can be formed from a hard ceramic rather than from punched "green" ceramic tapes. This can be done by drilling holes at the locations of the electrodes 28 and/or the electrical connections 30 using a laser or mechanical drill. The holes can then be filled with a paste or ink 36 as previously described, and heated to an elevated temperature (e.g. 850-1450° C.) to sinter the electrodes 28 and/or the electrical connections 30. An ultra-precision diamond turning machine can be used to provide a circular shape for the ceramic parts, and also to provide a predetermined radius for the lower major surface 18 of the ceramic base 14. The remainder of the processing to form the completed electrode array 10 can take place as previously described for the devices 10 described herein with reference to FIGS. 1-7.

Although the electrode array 10 of the present invention has been described with a circular shape in plan view, in other embodiments of the present invention, other shapes can be used for the electrode array 10 including elliptical, or polygonal. When the electrode array 10 is formed with an elliptical or polygonal shape, the lower major surface 18 of the ceramic base 14 will still preferably have a radius of curvature which is substantially identical to the curvature of the inner surface of a user's retina to provide an intimate contact therewith.

The matter set forth in the foregoing description and accompanying drawings is offered by way of illustration only and not as a limitation. The actual scope of the invention is intended to be defined in the following claims when viewed in their proper perspective based on the prior art.

What is claimed is:

1. An electrode array for neural stimulation, comprising:
   a two-part ceramic package further comprising a ceramic base and a ceramic lid, with the ceramic base and the ceramic lid each having a pair of major surfaces and with at least one of the ceramic base and the ceramic lid having a ceramic lip extending outward therefrom to define an interior region between the ceramic base and the ceramic lid, and with the ceramic lid having a plurality of electrical connections extending between the pair of major surfaces thereof, and with the ceramic base having a plurality of electrodes extending between the pair of major surfaces thereof; and
   an electronic circuit located within the interior region to receive electrical input signals conducted through the plurality of electrical connections and to generate therefrom electrical output signals which are communicated to the plurality of electrodes for use in neural stimulation.

2. The electrode array of claim 1 wherein the major surface of the ceramic base outside of the interior region is a curved surface.

3. The electrode array of claim 2 wherein the two-part ceramic package has a circular shape.

4. The electrode array of claim 1 wherein the ceramic base is attached to the ceramic lid by a metal-to-metal seal formed therebetween.

5. The electrode array of claim 1 further comprising a plurality of electrical interconnections extending between the electrical connections in the ceramic lid and a plurality of contact pads located on the electronic circuit or on the major surface of the ceramic base inside the interior region to further conduct the electrical input signals to the electronic circuit.

6. The electrode array of claim 1 wherein the electrodes comprise metal.

7. The electrode array of claim 1 wherein each electrode is overcoated with a layer of platinum on an exposed end thereof outside of the interior region.

8. The electrode array of claim 1 wherein the electrodes comprise sintered metal electrodes.

9. The electrode array of claim 1 wherein the electrodes comprise a sintered mixture of ceramic and metal.

10. The electrode array of claim 1 wherein the electronic circuit comprises a demultiplexer circuit.

11. The electrode array of claim 1 wherein the ceramic base and the ceramic lid are formed from a ceramic material which comprises 50-80 percent by volume zirconium oxide and 50-20 percent by volume aluminum oxide.

12. An electrode array for neural stimulation, comprising:
    a ceramic base having a first major surface and a second major surface, with the first major surface being curved, and with a ceramic lip located about a curved edge of the second major surface and extending towards the first major surface, and with a plurality of electrodes arranged in a two-dimensional array and extending through the ceramic base between the first and second major surfaces;
    a ceramic lid having a plurality of electrical connections extending therethrough, with the ceramic lid being attachable to the ceramic base to form a hermetically-sealed interior region; and
    an electronic circuit located within the hermetically-sealed interior region and having a plurality of input ports and a plurality of output ports, with the input ports being connected to the electrical connections in the ceramic lid, and with the output ports being connected to the electrodes in the ceramic base to provide electrical output signals to the electrodes for neural stimulation in response to electrical input signals provided to the input ports of the electronic circuit.

13. The electrode array of claim 12 wherein the ceramic base and ceramic lid are both circular in shape with a diameter, of a few millimeters.

14. The electrode array of claim 12 wherein the ceramic base and the ceramic lid comprise a ceramic material which further comprises 50-80 percent by volume zirconium oxide and 50-20 percent by volume aluminum oxide.

15. The electrode array of claim 12 wherein the first major surface has a surface radius of curvature which is adapted to provide contact with an inner surface of a human retina.

16. The electrode array of claim 12 wherein the electrodes comprise metal.

17. The electrode array of claim 12 wherein the electrodes comprise sintered metal electrodes.

18. The electrode array of claim 12 wherein the electrodes comprise a sintered mixture of ceramic and metal.

19. The electrode array of claim 12 wherein the electrodes are overcoated with a layer of platinum on at least one end thereof.

20. The electrode array of claim 12 wherein the electrical connections in the ceramic lid comprise metal.

21. The electrode array of claim 12 wherein each output port is connected to one of the electrodes in the ceramic base by solder.

22. The electrode array of claim 12 wherein each input port is connected to one of the electrical connections in the ceramic lid by solder.

23. The electrode array of claim 12 wherein each input port is connected to one of the electrical connections in the ceramic lid by an electrically-conductive epoxy.

24. The electrode array of claim 12 wherein each input port is connected to one of the electrical connections in the ceramic lid by an electrically-conductive spring.

25. The electrode array of claim 12 wherein each input port is connected to one of the electrical connections in the ceramic lid by a deformable metal pin.

26. The electrode array of claim 12 wherein each input port is connected to one of the electrical connections in the ceramic lid via a contact pad formed on the second major surface of the ceramic base.

27. The electrode array of claim 12 wherein the ceramic lid is attachable to the ceramic base by a metal annulus formed on the ceramic lip and another metal annulus formed on the ceramic lid, with the two metal annuluses being brazed together.

28. The electrode array of claim 27 wherein the ceramic lid comprises another ceramic lip extending outward from a major surface thereof towards the ceramic body, with the metal annulus on the ceramic lid being formed on the ceramic lip thereof.

29. The electrode array of claim 12 wherein the electronic circuit comprises a demultiplexer circuit.

30. An electrode array for neural stimulation comprising a two-part ceramic package having a ceramic base and a ceramic lid, with the ceramic base having a plurality of electrodes formed therein as a part of the ceramic base prior to the insertion of an electronic circuit into the two-part ceramic package, and with the ceramic lid having a plurality of electrical connections formed therein as a part of the ceramic lid prior to the insertion of the electronic circuit, and with at least one of the ceramic base and the ceramic lid having a ceramic lip extending outward therefrom to define an interior region between the ceramic base and the ceramic lid for insertion of the electronic circuit, and with the electronic circuit having input ports connected to the plurality of electrical connections to receive electrical input signals into the electronic circuit, and with the electronic circuit having output ports to provide output signals to the plurality of electrodes for neural stimulation.

31. The electrode array of claim 30 wherein the ceramic base is attached to the ceramic lid by a metal-to-metal seal formed therebetween.

32. The electrode array of claim 30 wherein the electronic circuit comprises a demultiplexer circuit.

* * * * *